United States Patent [19]

Chupp et al.

[11] Patent Number: 4,540,522

[45] Date of Patent: Sep. 10, 1985

[54] PREPARATION OF SUBSTITUTED BENZYLIC HALIDES

[75] Inventors: John P. Chupp, Kirkwood; Terry M. Balthazor, University City, both of Mo.

[73] Assignee: Monsanto Company, St. Louis, Mo.

[21] Appl. No.: 539,887

[22] Filed: Oct. 7, 1983

Related U.S. Application Data

[62] Division of Ser. No. 358,966, Mar. 17, 1982, abandoned.

[51] Int. Cl.$^3$ ................ C07C 121/78; C07C 87/60
[52] U.S. Cl. ..................... 260/465 E; 260/465 F; 560/47; 560/65; 560/218; 564/218; 564/441; 564/442; 568/655

[58] Field of Search ........... 260/465 G, 465 E, 465 F; 564/442, 218, 441; 560/47, 65; 568/655

[56] References Cited

PUBLICATIONS

Kwart et al., J. Am. Chem. Soc., vol. 93, 7250 (1971).

*Primary Examiner*—Dolph H. Torrence
*Attorney, Agent, or Firm*—Richard H. Shear; Robert B. Martin

[57] ABSTRACT

This invention pertains to processes for the preparation of nuclear substituted benzylic halides such as ortho-amino benzyl chlorides by reaction of substituted benzyl sulfoxides with nonoxidizing acid halides.

22 Claims, No Drawings

PREPARATION OF SUBSTITUTED BENZYLIC HALIDES

This is a division of application Ser. No. 358,966, filed Mar. 17, 1982, abandoned.

BACKGROUND OF THE INVENTION

1. Field of the Invention

This invention pertains to processes for the preparation of nuclear substituted benzylic halides such as ortho-amino benzyl chlorides by reaction of substituted benzylic sulfoxides with nonoxidizing acid halides.

2. Description of the Prior Art

Sulfoxides of the general formula RSOR are known to undergo rearrangements under acid conditions to produce alpha-substituted sulfides, the overall result being reduction of the sulfoxide group and oxidation of the adjacent carbon atom. Reactions of this type are generally known as the Pummerer reaction. The products of such Pummerer reactions when acid halides are employed normally include alpha-substituted halomethyl sulfides, or via hydrolysis, the corresponding aldehydes. Russell & Mikol, Mech. Mol. Migr., 1, 157–207 (1968).

Substituted ortho-amino benzyl chloride per se has been described in the prior art but this compound has been produced from the corresponding ortho-amino benzyl alcohol, and not from an amino benzyl sulfoxide.

It is an object of the present invention to provide a process for the conversion of nuclear substituted benzyl sulfoxides to nuclear substituted benzylic halides in good yields.

It is another object of this invention to provide novel ortho-amino benzyl halide compounds which are useful for the preparation of aniline derived herbicide compounds.

It is a further object of this invention to provide a process for making ortho-amino benzyl halide compounds which employs starting materials derived from known aromatic sulfilimine rearrangement products.

SUMMARY OF THE INVENTION

In accordance with the foregoing, and other objects which will readily occur to those skilled in the art, the present invention provides a process for the preparation of nuclear substituted benzyl halides which comprises reacting a nuclear substituted benzyl sulfoxide in the presence of an inert solvent with a nonoxidizing acid halide to produce a nuclear substituted benzyl halide, wherein said benzyl sulfoxide contains a nuclear substituent, ortho or para to the benzylic sulfoxide substituent, said nuclear substituent comprising an activating group having a Hammett sigma (para) constant which is more negative than about $-0.20$ and having sufficient electron donating properties to favor benzylic carbonium ion formation upon electrophic attack on sulfoxide.

The present invention also provides nuclear substituted ortho-amino benzyl halides (i.e., ortho-halomethyl anilines) such as 2-chloromethyl-6-trifluoromethyl aniline, which preferably are prepared from starting materials derived from ortho-methylthiomethyl anilines which in turn can be easily derived from the corresponding substituted aniline via known aromatic sulfilimine rearrangement.

DETAILED DESCRIPTION OF THE INVENTION

In the normal Pummerer reaction sulfoxides undergo rearrangement with nonoxidizing acid halides to give alpha-substituted halides and aldehydes. Applicants have discovered a reaction which can be characterized as an abnormal Pummerer reaction in which certain nuclear substituted benzylic sulfoxides react with the same nonoxidizing acid halides to form benzyl halides.

The nuclear substituent(s) on the benzylic sulfoxide are determinative whether the reaction proceeds via the normal or abnormal Pummerer route. The abnormal Pummerer reaction of the present invention proceeds via the formation of a benzylic carbonium ion intermediary. Accordingly, the primary nuclear substituent should be an activating group, i.e., electron donating, located ortho or para to the methyl sulfoxide substituent and having sufficient activation strength to stabilize the benzyl carbonium ion upon electrophilic attack. One good measure of this activity is the Hammett sigma (para) constant of the substituent. Sigma (para) is an approximate measure of the activating strength of a substituent in either the para or ortho position. In general to effect benzyl halide production via the nonoxidizing abnormal Pummerer route the primary nuclear substituent should have a sigma (para) that is more negative than about $-0.20$.

The preferred primary nuclear substituents having the above described characteristics are alkoxy groups and amino groups. $NH_2$ substituents which are ortho to the benzylic sulfoxide substituent are the most preferred.

The benzyl sulfoxide starting material may, if desired, contain 0–4 secondary nuclear substituents. In general, the selection of the secondary nuclear substituent, if any, is not critical to the reaction process of the present invention. Any activating, neutral or deactivating group(s) may be employed as long as it does not destabilize the benzylic carbonium ion intermediate induced by the presence of the chosen primary nuclear substituent. Among the suitable secondary nuclear substituents are alkyl, haloalkyl, alkoxy, polyalkoxy or alkoxyalkyl, alkenyl, alkenyloxy, alkynyl or alkynyloxy, aryl, aryloxy, aralkyl or aralkyloxy, amino, $NO_2$, CN, halogen, and saturated or unsaturated heterocyclic radical having up to 6 rings atoms containing O, S and/or N.

When the primary nuclear substituent is an amino group, preferred secondary nuclear substituents include haloalkyl, such as $CF_3$; alkyl, such as methyl or ethyl; alkoxy, such as methoxy or ethoxy; halogen, such as Cl or Br; carboalkoxy such as carbomethoxy; and CN. When the primary nuclear substituent is an alkoxy group, the preferred secondary nuclear substituents are alkyl or alkoxy. In the case of the preferred ortho-amino benzyl sulfoxide starting materials a preferred secondary nuclear substituent location is in the 6- position. In these materials the most preferred secondary nuclear substituent is $CF_3$.

In general the selection of any nuclear substituents should be made to avoid substituents that adversely interact with the solvents or reactants employed in the overall process described herein.

As used herein the term "benzyl sulfoxide" refers to sulfinyl compounds of the general formula $ArCH_2SOR_1$ where Ar is a substituted or unsubstituted phenyl radical and the $R_1$ substituent is any aryl or alkyl group as hereinafter defined which does not adversely affect the reaction of the present invention. Similarly, the term "benzyclic sulfoxide substituent" refers to radicals of the formula—$CH_2SOR_1$ where $R_1$ is as previously defined. Since this $R_1$ group is cleaved from the final product, simple and inexpensive alkyl substituents such as $CH_3$ are preferred.

The term "alkyl" refers to both straight chain and branched chain alkyl radicals. Preferred are alkyls containing 1 to 6 carbon atoms such as methyl, ethyl, n-propyl, isopropyl, n-butyl, isobutyl, sec-butyl, tertbutyl, n-pentyl, isopentyl, n-hexyl, sec-hexyl and the like.

The term "aryl" refers to both substituted and unsubstituted aromatic radicals such as phenyl, benzyl, tolyl, xylyl and the like.

The term "alkoxy" refers to both straight chain and branched chain alkoxy radicals containing alkyl, alkenyl and alkynyl groups as defined above.

The term "carboalkoxy" refers to the radicals of the formula $COOR_c$ where $R_c$ is an alkyl as defined above.

When used to described a primary nuclear substituent the term "amino" refers to radicals of the formula NHR' where R' is hydrogen or alkyl. The term "amino" when used as a secondary nuclear substituent refers to radicals of the formula NR"R'" where R" and R'" can be any of a variety of substituents of the type herein listed such as hydrogen, acyl, alkyl or aryl as defined above.

The term "alkenyl" refers to both straight chain and branched chain alkenyl groups of the type —$C_nH_{2n-1}$. Preferred are those alkenyl groups containing 3 to 5 carbon atoms.

The term "alkynyl" refers herein to a group of the type —$C_nH_{2n-3}$ and includes both straight chain and branched chain groups. Preferred are alkynyl groups containing 3 to 5 carbon atoms.

The term "alkoxyalkyl" refers to an alkyl group sustituted on the terminal carbon by an alkoxy group.

The term "haloalkyl" refers to an alkyl group substituted by one or more halogen atoms, e.g., chloromethyl, bromomethyl, dichloroethyl, trichloromethyl, trifluoromethyl, pentafluoroethyl, iodomethyl and the like.

The substituted benzyl sulfoxides useful as starting materials according to the present invention generally are known and can be prepared, for example, by oxidation of the corresponding benzyalkyl sulfide. See, e.g., Jackson U.S. Pat. No. 4,006,183; Claus, Mh Chem. Bd., 102, p. 1571-1582 (1971). The preferred starting sulfoxide materials are ortho-amino benzyl sulfoxides. Of particular interest in the process of the present invention are those ortho-amino benzyl sulfoxides derived from ortho-amino benzyl sulfides which have been producedby sulfilimine rearrangement from the corresponding substituted anilines. A typical sulfilimine rearrangement proceeds as follows: aniline is reacted with dimethyl sulfide in the presence of a base and oxidizing agent such as N-chlorosuccinimide to give an aromatic sulfilimine product having a —$N=S(CH_3)_2$ group. Such reactions are known in the art and are described, inter alia, in Gassman, Tetrahedron Letters, 497 (1972); Gassman, Tetrahedron Letters, 24, 2055-2058 (1977); Vilsmeier, Tetrahedron Letters 624 (1972); Jackson U.S. Pat. Nos. 3,966,371 and 4,006,183; and Claus, Mh Chem. Bd. 102, pp. 1571-1582 (1971). In a variation of the sulfilimine reaction, when a base such as sodium hydroxide is used, the neutralization can be accompanied by a conversion of by-product succinimide to an aqueous solution of sodium succinimide which can be regenerated to a chlorosuccinimide. The sulfilimine rearranges upon heating or catalysis to provide ortho-methylthiomethyl anilines which can in turn be oxidized, for example, with hydrogen peroxide to yield the starting ortho-methylsufinylmethyl anilines.

In carrying out the process of the present invention, the benzyl sulfoxide starting material is reacted with an acid halide. The term "acid halide" as used herein, refers to agents which are capable of liberating a halide ion (i.e., chloro, fluoro, bromo or iodo) in situ. An acid halide for the purposes of this invention can be chosen from a wide variety of acid derivatives such as those derived from sulfonic acids, phosphoric acids, phosphonic acids, and carboxylic acids having an organic moeity that may be alkyl haloalkyl, phenyl, benzyl or substituted derivates thereof. Included in this class of materials are acyl halides such as acetyl chloride, and haloacetyl halides such as chloroacetyl chloride. Acid halides also, of course, include hydrogen halides and, indeed, hydrogen chloride is a preferred acid halide. In general, acid halides used in the normal Pummerer reaction can be employed in the abnormal Pummerer reaction described herein.

In certain circumstances it is possible to produce the benzyl sulfoxide in situ by starting with the corresponding benzyl sulfide, for example, by oxidation with hydrogen peroxide or similar materials. One particularly useful method, which takes advantage of the abnormal Pummerer reaction of the present invention without actually isolating or starting with the benzyl sulfoxide, is based on the cyclic sulfilimine formation which can be effected employing ortho-amino benzyl sulfide substrates. According to this process, ortho-amino benzyl sulfides can be reacted with a halogenating agent such as chlorine or sulfuryl chloride to produce a cyclic sulfilimine salt and hydrogen chloride, which upon addition to stoichiometric amounts of water, hydrolizes to the sulfoxide and hydrogen chloride. The sulfoxide and hydrogen halide formed in situ can be reacted as described above without isolating a sulfoxide or without the need to add additional hydrogen halide to produce the ortho-amino benzyl halide in a single reaction vessel. (Addition of hydrogen halide directly to the cyclic sulfilimine without adding water first, will not give the benzyl halide product.) This route is also advantageous since the procedure does not introduce large quantities of water into the system as does the route employing hydrogen peroxide to oxidize the sulfides to the sulfoxides.

When the acid halide is a haloacyl halide, such as chloroacetyl chloride and the primary nuclear substituent is an amino group (NHR'), reaction of the ortho-amino benzyl sulfoxide with excess chloroacetyl chloride gives an abnormal Pummerer reaction product (e.g., ortho-amino benzyl chloride) containing an N-chloroacetyl group. Other haloacetyl halides also provide similar results. Such compounds are particularly desirable starting materials for the production of alpha-halo acetanilide herbicides.

The abnormal Pummerer reaction of a benzyl sulfoxide with an acid halide is carried out in an appropriate solvent. In general the solvent should be substantially inert to the reactants or products formed and should possess appropriate solubility for the reactants and products. Included in this class of solvents are hydrocarbons, halohydrocarbons, ethers and the like. Representative solvents include carbon tetrachloride, toluene, xylene, chlorobenzene, chloroform, methylene chloride, ethylene dichloride, trichloroethane. A preferred solvent is ethylene dichloride.

The ratios of reactants in the above-described process are dictated primarily by economic considerations and avoidance of unwanted by-products. Hence, large excesses or deficiencies of any expensive component relative to another component should be avoided and essentially stoichiometric ratios are often preferred. Concentrations of reactants employed can affect product yield. In general, reactant concentrations of from about 0.1 M up to about 1.5 M can be employed and yields tend to be optimum at or near approximately .5 M concentration.

The process of this invention may be carried out at any convenient temperature ranging from 0° C. to ambient or higher. Thus, reaction temperatures of from about 0° to about 200° C. can be broadly employed. In practice, however, it is preferred to employ reaction temperatures in the range of from about 40° to about 120° C. with about 50° to about 85° C. being the most preferred reaction temperature range. The process may be carried out at any convenient pressure, either above or below atmospheric; however, for practical considerations atmospheric conditions are preferred. The reaction proceeds rapidly. The choice of temperatures, pressures, equipment and the like to suit any particular set of reactants is within the skill of the art. The process may, of course, be carried out either batchwise or continuously.

In the preferred embodiment, the sulfoxide reactant is dissolved in the inert solvent with mixing and gaseous acid halide reagent is admitted, e.g., bubbled, through the mixture. In most cases it is desirable to remove water at the end of the reaction by distilling the reaction product until the product is essentially anhydrous.

The resulting benzyl halide product is stable while dissolved in the solution. Neutral products can be recovered by washing the reaction mixture with water and product isolation accomplished by solvent separation and removal. Since the ortho-amino benzyl halide products described herein have a tendency to polymerize if the solvent is removed, it is preferred to recover these materials as the aniline hydrogen halide salts (anilinium salts). This can be effected by treating the benzyl halide solution with hydrogen halide and stirring. Since many of the anilinium salts are formed only at low temperatures, it is preferred to cool the benzyl halide solution to about 0° to 5° C. during the hydrogen halide treatment. The precipitation and filtration of the anilinium salt results in salt yields of up to 95% or more and results in a product which is substantially free from sulfur-containing abnormal Pummerer reaction by-products such as $CH_3SO_2SCH_3$ and $CH_3SH$. The anilinium salt can be neutralized and dissolved as an essentially pure compound in an organic solvent for further handling or processing.

The preferred compounds produced by the process of this invention are ortho-amino benzyl halides having at least one secondary nuclear substituent selected from the group consisting of $CF_3$, CN, Cl, $CH_3$, $CH_2CH_3$, $OCH_3$ and $CO_2CH_3$. The most preferred compounds are: 2-chloromethyl-6-trifluoromethyl aniline; 2-chloromethyl-6-cyano aniline; 2-chloromethyl-6-methyl aniline; 2-chloromethyl-6-ethyl aniline; 2-chloromethyl-6-methoxy aniline; 2-chloromethyl-6-carbomethoxy aniline; 2-chloromethyl-5-chloro-6-methoxy aniline; and the HX salts (anilinium salts) of each of the foregoing anilines; 2'-chloromethyl-6'-trifluoromethyl acetanilide; 2-chloro-2'-chloromethyl-6'-trifluoromethyl acetanilide.

The claimed compounds find particular utility in the preparation of herbicide compounds. Upon catalytic hydrodehalogenation the claimed ortho-amino benzyl halide can be converted to 2-methyl anilines, such as 2-methyl-6-(trifluoromethyl) aniline. Examples of such methods are described in the following commonly assigned copending applications filed concurrently herewith: Chupp and Balthazor application Ser. No. 358,772, entitled "Manufacture of Ortho-Methyl Anilines From Ortho-Amino Benzyl Sulfoxides" and; Miller and Chupp application Serial No. 358,773, entitled "Preparation of Ortho-Methyl Anilines From Ortho-Amino Benzyl Sulfoxides." The 2-methyl anilines can be converted to 2-halo acetanilide herbicide compounds by methods described in commonly assigned, copending Chupp application Ser. No. 333,345, entitled "Herbicidal 2-Haloacetanilides", filed Dec. 22, 1981, abandoned.

The following examples are for the purposes of illustrating the invention in greater detail and are not intended as a limitation upon the scope thereof.

EXAMPLE 1

This example demonstrates the reaction of benzyl methyl sulfoxide with anhydrous HCl via normal Pummerer reaction (i.e., the prior art method).

A solution of 1.5 grams (9.7 mol) of benzyl methyl sulfoxide in 15 ml of carbon tetrachloride was heated with stirring to reflux with bubbling HCl through. Upon cooling the reaction product NMR and GC assays indicate two reaction products: benzyladehyde (60%) and benzyl methyl sulfide (40%). The structures of these normal Pummerer products were confirmed by GC and MS analysis.

EXAMPLE 2

This example demonstrates that the procedure of Example 1 produces an abnormal Pummerer product (4-methoxy benzyl chloride) when a benzyl sulfoxide contains a primary nuclear activating substituent (methoxy).

A solution of 1 gram of 4-methoxy benzyl sulfoxide in 10 ml of carbon tetrachloride was heated to reflux. Anhydrous HCl gas was passed through the solution for 15 minutes and the solvent was then removed to give a slightly pink liquid. This product was shown by GC-MS analysis and comparison (via NMR and GLC) with authentic material to be 2-chloromethyl-4-methoxy aniline. The yield was calculated at 100% with 90% conversion.

EXAMPLE 3

This example demonstrates a preferred method for the preparation of 2-chloromethyl-6-trifluoromethyl aniline HCl.

A solution of 200 grams (.0844 mol) of 2-methylsulfinylmethyl-6-trifluoromethyl aniline in 250 ml of ethylene dichloride in a 500 ml round bottom flask equipped with an efficient stirrer, and HCl inlet tube, distilling head and thermometer was treated at room temperature with gaseous HCl until the initial tacky precipitate gave way to a cloudy mixture (3–5 minutes). The mixture was then heated rapidly to 60°–63° C. while HCl is bubbled through the mixer. After 10 minutes of heating and HCl treatment, 1 ml of $H_2O$ was added, and heating and HCl treatment were continued until the mixture becomes clear (generally 10–15 minutes after H₂O addition)(a very small amount of insoluble material observed on the sides of the flask at this point). The clear orangish solution was then further heated (the HCl was stopped at this point) and solvent and H₂O were distilled off until no H₂O remains in the reaction flask (typically 50–60 ml of solvent were removed over 15–20 minutes). The clear yellow solution was then cooled, with stirring and HCl bubbling through, to 0° to 5° C. The precipitated solid was collected by filtration and washed with 50 ml of cold ethylene dichloride, then sucked as dry as possible. Yield of off-white ammonium benzylchloride was typically 95%, (contains a small amount of water). This material has a melting point of about 70°–75° C. Analysis Calculated for $C_8H_8Cl_2F_3N$: C, 39.05; H, 3.28; N, 5.69; Found: C, 41.36; H, 3.43; N, 5.98.

EXAMPLES 4–8

Procedures analogous to those described in Example 3 were used to prepare the various 2-chloromethyl anilinium hydrochloride salts listed in the following table along with selected properties of these materials.

TABLE 1

| Ex. No. | Product | mp °C. | % Yield | Empirical Formula | Analysis Cal'c. | Found |
|---|---|---|---|---|---|---|
| 3. | 2-chloromethyl-6-ethyl anilinium hydrochloride | 128 | 86.1 | $C_9H_{13}Cl_2N$ | C 52.44<br>H 6.37<br>N 6.80 | 52.18<br>6.43<br>6.77 |
| 4. | 2-chloromethyl-6-methyl anilinium hydrochloride | 190–205 | 8794 | $C_8H_{11}Cl_2N$ | C 50.02<br>H 5.78<br>N 7.29 | 49.83<br>5.59<br>6.93 |
| 5. | 2-chloromethyl-6-methoxy anilinium hydrochloride | 100 | 83.3 | $C_8H_{11}Cl_2NO$ | C 46.17<br>H 5.34<br>N 6.73 | 46.16<br>5.33<br>6.78 |
| 6. | 2-chloromethyl-6-carbomethoxy anilinium hydrochloride | 130–225 | 95.5 | $C_9H_{11}Cl_2NO_2$ | C 45.78<br>H 4.70<br>N 5.93 | 45.68<br>4.62<br>5.88 |
| 7. | 5-chloro-6-methoxy anilinium hydrochloride | 165–230 | 94.4 | $C_8H_{10}Cl_3NO$ | C 39.61<br>H 4.16<br>N 5.78 | 39.02<br>4.09<br>5.56 |
| 8. | 2-chloromethyl anilinium hydrochloride | — | 92.3 | $C_7H_9Cl_2N$ | C 47.21<br>H 5.10<br>N 7.87 | 47.22<br>5.16<br>7.75 |

EXAMPLE 9

This example demonstrates the preparation of 2′-chloromethyl-6′-trifluoromethyl acetanilide.

7.8 grams (.10 mol) of acetylchloride was heated at reflux in about 100 ml of toluene with 12 grams (0.05 mol) of 2-methylsulfinylmethyl-6-trifluoromethyl aniline. After evaporation of solvent, HPLC with 15% ethylacetate, 85% cyclohexane, fractions 38–53 gave 3.2 grams of product with fraction 42 recrystallized from methylcylcohexene/ethylacetate to give 2′-chloromethyl-6′-trifluoromethyl acetanilide. This material had a melting point of 137°–140° C. Analysis Calculated for $C_{10}H_9ClF_3NO$: C, 47.73; H, 3.61; N, 5.57; Found: C, 47.55; H, 3.57; N, 5.48.

EXAMPLE 10

This example demonstrates an alternative method for preparation of 2-chloromethyl-6-trifluoromethyl aniline HCl.

Chlorine (7.60 grams, 1.07 (mol) was bubbled into a mechanically stirred solution of 221.0 grams (1.00 mol) of 2-methylthiomethyl-6-trifluoromethyl aniline in 2 liters of ethylene dichloride over 60 minutes while maintaining the reaction temperature below 20° C. A white suspension formed initially, became very thick halfway through the addition, and dissolved to give way to a cloudy solution at the end of the addition. The mixture was then heated to 60° C. while maintaining a steady stream of HCl bubbling through. Water (25 ml, 1.4 mol) was added and the HCl treatment was maintained at 60° C. for 15 minutes at which point a clear solution was obtained. Excess water was removed by azeotropic distillation (780 ml of solvent were removed) and the resulting solution was cooled to 0° C. with a steady stream of HCl bubbling through. Filtration, washing of the solids with 150 ml of cold ethylene dichloride and air-drying gave 228.0 grams (92.7%) of off-white 2-chloromethyl-6-trifluromethyl anilinium hydrochloride. This compound properties and analysis are described above.

EXAMPLE 11

In a variation on the procedure of Example 10, HCl was not introduced into the reaction mixture until time for precipitation of the anilinium salt. Chlorine (6 grams, 0.084 mol) was passed into a solution of 17.5 grams (0.0792 mol) of 2-methylthiomethyl-6-trifluoromethyl aniline in 160 ml of ethylene dichloride at 15°–21° C. over a 15 minute period. Water (2 ml, 0.11 mol) was added and the cloudy solution was heated to 63° C. The mixture was maintained at 63° C. and after 30 minutes a clear solution was obtained. Excess water was removed by azeotropic distillation (65 ml of solvent were removed) and the solution was cooled to 0° C. with a stream of HCl bubbling through. The resulting solid anilinium salt was isolated by filtration yielding 17.7 grams (90.9%).

EXAMPLE 12

This example demonstrates a process for the preparation of 2-amino 3-chloromethyl benzonitrile.

38.85 grams (0.2 mol) of 2-amino 3-methylsulfinylmethyl benzonitrile was combined with 500 ml of ethylene dichloride in a 1 L. flask equipped with mechanical stirrer, reflux condenser, thermometer and gas inlet. HCl gas was bubbled through. A thick, dark yellow then a sticky dark orange semi-solid separated. Upon continued addition, the semi-solid went slowly back to give a cloudy orange mixture. Temperature rose to 35° C. over 10 to 15 minutes with high speed stirring near the end of the process. Upon continued bubbling of HCl with heating to 60°–65° C. for 10 minutes a solid had formed. Two mls of H₂O was added with continued slow HCl passage at 60°–65° C. After 20 minutes a good deal of sticky solid has been obtained. The apparatus was switched to the distilling head, the temperature increased and H₂O azeotrope was distilled off (about 125 ml distilled off). The resulting mixture was cooled in an ice bath with continued HCl passage whereby a yellow solid formed. This was washed with 100 ml of cold ethylene dichloride and dryed in vacuo. The product was the hydrochloride salt of 2-amino 3-chloromethyl benzonitrile.

Since modifications will be apparent to those skilled in the art, it is intended that this invention be limited only by the scope of the appended claims.

We claim:

1. A process for the preparation of nuclear substituted benzyl halides which comprises reacting a nuclear substituted benzyl alkyl sulfoxide in the presence of an inert solvent with a nonoxidizing acid halide to produce a nuclear substituted benzyl halide, wherein said benzyl alkyl sulfoxide contains an activating nuclear substituent, ortho or para to the benzylic sulfoxide substituent, said nuclear substituent comprising an activating group having a Hammett sigma (para) constant which is more negative than about −0.20 and having sufficient electron donating properties to stabilize the benzylic carbonium ion upon electrophilic attack on the sulfoxide.

2. The process of claim 1 wherein said activating nuclear substituent is selected from the group consisting of amino and alkoxy radicals.

3. The process of claim 2 wherein said amino radical is NH₂ group located ortho to said benzyl alkyl sulfoxide substituent.

4. The process of claim 3 wherein said benzyl alkyl sulfoxide is formed in situ by reacting a methylthiomethyl aniline with a halogenating agent to produce an aromatic cyclic sulfilimine intermediate which is rearranged with the addition of water to provide said benzyl alkyl sulfoxide.

5. The process of claim 4 wherein said methylthiomethyl aniline is derived from a corresponding aniline via a sulfilimine rearrangement reaction.

6. The process of claim 1 wherein said benzylic sulfoxide substituent is a methylsulfinylmethyl group.

7. The process of claim 1 wherein said benzyl alkyl sulfoxide contains at least one secondary nuclear substituent which does not interfere with the ability of said activating nuclear substituent.

8. The process of claim 7 wherein said secondary nuclear substituent is selected from the group consisting of CF₃, CN, halogen, alkyl, alkoxy, and carboalkoxy.

9. The process of claim 1 wherein said nonoxidizing acid halide is selected from the group consisting of acylhalides, haloacylhalides and inorganic acid halides.

10. The process of claim 9 wherein said nonoxidizing acid halide is selected from the group consisting of HCl, acetyl chloride and chloroacetyl chloride.

11. The process of claim 10 wherein said benzyl halide is an ortho-amino benzyl chloride.

12. The process of claim 1 wherein said inert solvent is a hydrocarbon, chlorohydrocarbon or ether.

13. The method of claim 12 wherein said solvent is ethylene dichloride.

14. The process of claims 3, 4 or 5 wherein said benzyl halide is 2-chloromethyl-6-trifluoromethyl aniline.

15. The process of claims 3, 4 or 5 wherein said benzyl halide is 2-chloromethyl-6-cyano aniline.

16. The process of claims 3, 4 or 5 wherein said benzyl halide is 2-chloromethyl-6-methyl aniline.

17. The process of claims 3, 4 or 5 wherein said benzyl halide is 2-chloromethyl-6-ethyl aniline.

18. The process of claims 3, 4 or 5 wherein said benzyl halide is 2-chloromethyl-6-methoxy aniline.

19. The process of claims 3, 4 or 5 wherein said benzyl halide is 2-chloromethyl-6-carbomethoxy aniline.

20. The process of claims 3, 4 or 5 wherein said benzyl halide is 2-chloromethyl-5-chloro-6-methoxy aniline.

21. The process of claims 3, 4 or 5 wherein said benzyl halide is 2'-chloromethyl-6'-trifluoromethyl acetanilide.

22. The process of claims 3, 4 or 5 wherein said benzyl halide is 2-chloro-2'-chloromethyl-6'-trifluoromethyl acetanilide.

* * * * *